United States Patent [19]

Dallmier et al.

[11] Patent Number: 6,136,205
[45] Date of Patent: *Oct. 24, 2000

[54] PROCESS TO MANUFACTURE STABILIZED ALKALI OR ALKALINE EARTH METAL HYPOBROMITE AND USES THEREOF IN WATER TREATMENT TO CONTROL MICROBIAL FOULING

[75] Inventors: Anthony W. Dallmier, Aurora; William F. McCoy; Shunong Yang, both of Naperville, all of Ill.

[73] Assignee: Nalco Chemical Company, Naperville, Ill.

[*] Notice: This patent is subject to a terminal disclaimer.

[21] Appl. No.: 09/305,892

[22] Filed: May 5, 1999

Related U.S. Application Data

[62] Division of application No. 08/904,375, Aug. 1, 1997, Pat. No. 5,942,126.

[51] Int. Cl.[7] ........................................ C02F 1/76
[52] U.S. Cl. .................. 210/754; 210/758; 210/764; 422/14; 8/107; 8/109; 8/129; 8/137
[58] Field of Search ................... 210/749, 754, 210/758, 764; 422/14; 423/511, 579; 8/107, 108.1, 109, 129, 115.68, 115.69, 137; 252/186.1, 186.21, 186.36, 186.37, 187.1

[56] References Cited

U.S. PATENT DOCUMENTS

| | | |
|---|---|---|
| 3,170,883 | 2/1965 | Owen et al. . |
| 3,328,294 | 6/1967 | Self et al. . |
| 3,558,503 | 1/1971 | Goodenough et al. . |
| 3,749,672 | 7/1973 | Golten et al. . |
| 3,767,586 | 10/1973 | Rutkiewic . |
| 4,096,029 | 6/1978 | Mills . |
| 4,241,080 | 12/1980 | Burk . |
| 4,451,376 | 5/1984 | Sharp . |
| 4,642,194 | 2/1987 | Johnson . |
| 4,693,894 | 9/1987 | Juda et al. . |
| 4,711,724 | 12/1987 | Johnson . |
| 4,759,852 | 7/1988 | Trulear . |
| 4,929,424 | 5/1990 | Meier et al. . |
| 5,076,952 | 12/1991 | Ahmed et al. . |
| 5,112,530 | 5/1992 | Baur et al. . |
| 5,424,032 | 6/1995 | Christensen et al. . |
| 5,476,670 | 12/1995 | Hight et al. . |
| 5,525,241 | 6/1996 | Clavin et al. . |
| 5,662,940 | 9/1997 | Hight et al. . |

FOREIGN PATENT DOCUMENTS

WO 97/20909  6/1997  WIPO .

Primary Examiner—Duane Smith
Assistant Examiner—Betsey Morrison Hoey
Attorney, Agent, or Firm—Kelly L. Cummings; Thomas M. Breininger

[57] ABSTRACT

The invention is a method for preparing a stabilized aqueous alkali or alkaline earth metal hypobromite solution. The method comprises the steps of:

a. Mixing an aqueous solution of alkali or alkaline earth metal hypochlorite having from about 5 percent to about 70 percent available halogen as chlorine with a water soluble bromide ion source;

b. Allowing the bromide ion source and the alkali or alkaline earth metal hypochlorite to react to form a 0.5 to 70 percent by weight aqueous solution of unstabilized alkali or alkaline earth metal hypobromite;

c. Adding to the unstabilized solution of alkali or alkaline earth metal hypobromite an aqueous solution of an alkali metal sulfamate in a quantity to provide a molar ratio of alkali metal sulfamate to alkali or alkaline earth metal hypobromite is from about 0.5 to about 7; and, d. Recovering a stabilized aqueous alkali or alkaline earth metal hypobromite solution.

8 Claims, No Drawings

PROCESS TO MANUFACTURE STABILIZED ALKALI OR ALKALINE EARTH METAL HYPOBROMITE AND USES THEREOF IN WATER TREATMENT TO CONTROL MICROBIAL FOULING

REFERENCE TO RELATED PATENT

The present application is a divisional of application Ser. No. 08/904,375, filed Aug. 1, 1997, by Anthony W. Dallmier and William F. McCoy, now U.S. Pat. No. 5,942,126, issued Aug. 24, 1999, entitled "Process to Manufacture Stabilized Alkali or Alkaline Earth Metal Hypobromite and Uses thereof in Water Treatment to Control Microbial Fouling", the disclosure of which is incorporated herein by reference.

FIELD OF THE INVENTION

The present invention relates to a method of preparing a stabilized alkali or alkaline earth metal hypobromite to control microbiofouling, more specifically, a stabilized sodium hypobromite solution the characteristics of which include non-volatility, high free halogen residual, lower bromate formation, reduced generation of absorbable organic halogen in process waters, as well as improved performance against biofouling.

BACKGROUND OF THE INVENTION

Aqueous solutions of sodium hypochlorite are widely used in cooling water towers; bleaching processes; treatment of recreational waters including swimming pool water, water slide and other water game equipment, spas, and whirlpools; disinfectants; laundry detergents; and, industrial biocides including applications in the petroleum industry. However, a major disadvantage of NaOCl is its instability. As is well known in the art, several methods are used to stabilize NaOCl. The Self et al. reference (U.S. Pat. No. 3,328,294) described a continuous process to stabilize hypochlorite with an equal molar ratio of sulfamic acid. This process was improved upon by Rutkiewic reference (U.S. Pat. No. 3,767,586) who added a buffer which aided in pH control increasing the stability of concentrated solutions.

Bromine has various advantages over chlorine for water treatment such as better performance in high pH or amine environments and a lower volatility. However, sodium hypobromite, the bromine analog to chlorine bleach, is not stable under typical storage conditions, and as such, is not commercially available. Instead, bromine is typically delivered to water treatment systems by various inefficient or inconvenient methods. The art described by either Self et al. or Rutkiewic does not mention a method to stabilize the well known precarious sodium hypobromite molecule as disclosed within this invention. Also, this disclosure shall improve upon the art of Rutkiewic by formulating a more stable, concentrated NaOBr solution in the absence of a buffer.

In one such bromine delivery method, NaBr is oxidized in situ by introducing gaseous chlorine or NaOCl into the process water stream. Another technique uses a stable perbromide ($Br_3$—) solution containing 30–40 percent bromine. The perbromide solution releases bromide and bromine when injected into water systems. The formed bromine hydrolyzes instantly to hypobromous and hydrobromic acids. Alternatively, bromine chloride may be added to aqueous process streams wherein it hydrolyzes to hypobromous and hydrochloric acids.

All of these bromine delivery systems have inherit disadvantages. Gaseous chlorine, perbromide, and bromine chloride have high halogen vapor pressures which present safety concerns in handling and storage. Also, these concentrated halogen solutions are corrosive to many metal surfaces found in process equipment either by their high vapor pressures or by the release of one mole of hydrohalic acids in water systems yielding localized low pH environments. As such, none of these methods provide a stable bromine product that can be safely and easily handled while meeting environmental requirements (more fully discussed below), such as low bromate and absorbable organic halogen generation, and having a high free halogen residual and a low volatility (resulting in a greatly reduced odor and vapor-phase corrosion). In addition, a portion of the expensive bromine compound is wasted through an ineffective by-product in some delivery schemes. Thus, the need for a safe, convenient, economical, stable bromine water treatment product remains and is significant.

The Goodenough et al. reference (U.S. Pat. No. 3,558,503), teaches stabilization of bromine using any compound which reacted reversibly with bromine. The disclosed compounds include:

(a) water-soluble primary and secondary amines or amides; and, (b) sulfamic acid and its water-soluble salts.

However, the bromine solutions prepared according to the Goodenough et al. reference teachings are not stable enough for practical use in commercial cooling water, oil field and other industrial applications.

Sulfamic acid, according to the Goodenough et al. reference, is employed as a free acid or as one of its water-soluble salts such as the sodium, potassium or ammonium salt. However, the manner in which the bromine solutions are prepared provide relatively low stabilities and low available halogen concentrations compared with the discoveries claimed within this invention disclosure. The Goodenough et al. reference charges elemental bromine into aqueous solution prior to stabilization. Because elemental bromine is used in the process disclosed in the Goodenough et al. reference, this process is difficult to complete as well as potentially hazardous since elemental bromine is a fuming, corrosive, toxic liquid.

The Goodenough et al. reference mentions that the available bromine concentration immediately following preparation was about 1 percent by weight. The low bromine concentration achieved by this method was due in part to bromine being soluble at just 4 percent in cold water. Additionally, bromine is wasted in the process disclosed in the Goodenough et al. reference. The reaction according to this process is as follows:

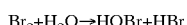

$$Br_2 + H_2O \rightarrow HOBr + HBr$$

Because the produced HBr does not function as a biocide, one half of the bromine adds nothing to the strength of the biocidal species, HOBr. This invention disclosure improves on the Goodenough et al. reference by means of a safer, easier, and more economical process.

Much higher levels of available halogen for disinfection were attained using the invention disclosed in this application, as shown in Table I below, by stabilizing the sodium salt (NaOBr) generated during manufacture. As previously mentioned, sodium hypobromite is unstable and therefore not commercially available. If a stabilized form of NaOBr is proposed, the stabilization process must occur quickly after NaOBr is made.

The method described in the Goodenough et al. reference could not achieve these increased bromine levels as the order of reagent addition described in the reference was deemed not critical to the operability of the method. Since NaOBr is synthesized by the following reaction, NaOCl+ NaBr→NaOBr+NaCl, addition of the stabilizer prior to bromide oxidation would not permit the formation of NaOBr.

When water is treated with many halogenated biocides, undesirable halogenated organics can be generated as by-products. These compounds are causing increased environmental and health concerns. It is generally known that low molecular weight halogenated organics are more easily biologically degraded than higher molecular weight species. However, the low molecular weight forms may be more toxic to aquatic and mammalian organisms. Differentiation of these halogenated organics is costly, time consuming and requires the use of gas chromatography, high performance liquid chromatography or gel permeation chromatography. Absorbable Organic Halogen, "AOX", was chosen as a method of measuring the sum of halogenated organic compounds without speciation. AOX is used as an effluent monitoring parameter of water or wastewater in Europe and North America. In the United States, the Environmental Protection Agency ("EPA") is looking closely at AOX discharge in the pulp and paper industry. An object of the present invention is to provide a stable NaOBr solution that can be used to control microbial fouling with minimal AOX generation. The problems associated with controlling AOX levels, being a more recent developing environmental concern, have not been previously resolved in the industry.

The United States EPA extrapolates some animal carcinogenesis with the presence of low bromate levels found in drinking water. Bromate may appear from the ozonation of bromide-containing water raising some concerns in the drinking water industry. Bromate may also be formed by the disproportionation of hypobromite. This reaction occurs at a greater rate in alkaline environments. Hence, if bleach is added to a NaBr solution, the high pH environment could lead to the undesirable production of bromate. One use of the present invention, which was previously unknown and is surprising, is to greatly minimize bromate formation by stabilizing hypobromite when conditions are favorable for bromate production.

The petroleum industry experiences biological problems, including microbiologically influenced corrosion, both localized and general, in oil field waters. In addition, bacteria can plug the wellbore surface in waterflood injection wells. The bacteria form slime plugs, reducing injectivity. Treatment with stable bromine water is a convenient method of dealing with these and similar problems.

It is an object of the present invention to provide a process whereby aqueous solutions of sodium hypobromite can be produced which are relatively resistant to degradation and/or decomposition and which are relatively non-corrosive and non-volatile, yet which retain an improved capacity for oxidation and bactericidal activity.

Another object of the present invention is to provide a stable sodium hypobromite solution in which the formation of AOX is minimized while providing improved microbial fouling control. Other objects and advantages of the present invention will become obvious from the following description thereof.

SUMMARY OF THE INVENTION

The invention, according to one embodiment is a method for preparing a stabilized aqueous alkali or alkaline earth metal hypobromite solution. The method comprises the steps of:

a. Mixing an aqueous solution of alkali or alkaline earth metal hypochlorite having from about 5 percent to about 70 percent available halogen as chlorine with a water soluble bromide ion source;

b. Allowing the bromide ion source and the alkali or alkaline earth metal hypochlorite to react to form a 0.5 to 70 percent by weight aqueous solution of unstabilized alkali or alkaline earth metal hypobromite;

c. Adding to the unstabilized solution of alkali or alkaline earth metal hypobromite an aqueous solution of an alkali metal sulfamate in a quantity to provide a molar ratio of alkali metal sulfamate to alkali or alkaline earth metal hypobromite is from about 0.5 to about 7; and, d. Recovering a stabilized aqueous alkali or alkaline earth metal hypobromite solution.

DESCRIPTION OF THE PREFERRED EMBODIMENTS

One embodiment of the invention is a method for preparing a stabilized aqueous alkali or alkaline earth metal hypobromite solution. The method comprises the steps of:

a. Mixing an aqueous solution of alkali or alkaline earth metal hypochlorite having from about 5 percent to about 70 percent available halogen as chlorine with a water soluble bromide ion source;

b. Allowing the bromide ion source and the alkali or alkaline earth metal hypochlorite to react to form a 0.5 to 70 percent by weight aqueous solution of unstabilized alkali or alkaline earth metal hypobromite;

c. Adding to the unstabilized solution of alkali or alkaline earth metal hypobromite an aqueous solution of an alkali metal sulfamate in a quantity to provide a molar ratio of alkali metal sulfamate to alkali or alkaline earth metal hypobromite is from about 0.5 to about 7; and, d. Recovering a stabilized aqueous alkali or alkaline earth metal hypobromite solution.

The alkali or alkaline earth metal hypochlorite is selected from the group consisting of sodium hypochlorite, potassium hypochlorite, magnesium hypochlorite, lithium hypochlorite, and calcium hypochlorite. The amount of hypochlorite used will vary depending upon which hypochlorite salt is used.

The bromide ion source is selected from the group consisting of sodium bromide, potassium bromide, lithium bromide, and hydrobromic acid. As shown in the examples, in a more preferred embodiment, the alkali or alkaline earth metal hypochlorite is sodium hypochlorite, the bromide ion source is sodium bromide, and the alkali or alkaline earth metal hypobromite is sodium hypobromite.

The aqueous solution of unstabilized alkali or alkaline earth metal hypobromite may contain from about 0.5 to about 70 percent by weight alkali or alkaline earth metal hypobromite, more preferrably from about 1 to about 30 percent by weight alkali or alkaline earth metal hypobromite, and most preferrably from about 4 to about 15 percent by weight alkali or alkaline earth metal hypobromite.

The pH of the stabilized aqueous alkali or alkaline earth metal hypobromite solution is from about 8 to about 14 and more preferrably from about 11 to about 14. The the molar ratio of the alkali metal sulfamate to the sodium hypobromite is preferrably from about 0.5 to about 7, more preferrably from about 0.5 to about 4, and most preferrably from about 0.5 to about 2.

Another embodiment of the invention is a stabilized aqueous solution of an alkali or alkaline earth metal hypobromite which is prepared by the steps of:

a. Mixing an aqueous solution of alkali or alkaline earth metal hypochlorite having from about 5 percent to about 70 percent available halogen as chlorine with a water soluble bromide ion source;

b. Allowing the bromide ion source and the alkali or alkaline earth metal hypochlorite to react to form a 0.5 to 30 percent by weight aqueous solution of unstabilized alkali or alkaline earth metal hypobromite;

c. Adding to the unstabilized solution of alkali or alkaline earth metal hypobromite an aqueous solution of an alkali metal sulfamate in a quantity to provide a molar ratio of alkali metal sulfamate to alkali or alkaline earth metal hypobromite is from about 0.5 to about 7; and, d. Recovering a stabilized aqueous alkali or alkaline earth metal hypobromite solution.

The alkali or alkaline earth metal hypochlorite is selected from the group consisting of sodium hypochlorite, potassium hypochlorite, magnesium hypochlorite, lithium hypochlorite, and calcium hypochlorite. The amount of hypochlorite used will vary, depending upon which hypochlorite salt is used.

The bromide ion source is selected from the group consisting of sodium bromide, potassium bromide, lithium bromide, and hydrobromic acid. As shown in the examples, in a more preferred embodiment, the alkali or alkaline earth metal hypochlorite is sodium hypochlorite, the bromide ion source is sodium bromide, and the alkali or alkaline earth metal hypobromite is sodium hypobromite.

The aqueous solution of unstabilized alkali or alkaline earth metal hypobromite may contain from about 0.5 to about 70 percent by weight alkali or alkaline earth metal hypobromite, more preferrably from about 1 to about 30 percent by weight alkali or alkaline earth metal hypobromite, and most preferrably from about 4 to about 15 percent by weight alkali or alkaline earth metal hypobromite.

The pH of the stabilized aqueous alkali or alkaline earth metal hypobromite solution is from about 8 to about 14 and more preferrably from about 11 to about 14. The the molar ratio of the alkali metal sulfamate to the sodium hypobromite is preferrably from about 0.5 to about 7, more preferrably from about 0.5 to about 4, and most preferrably from about 0.5 to about 2.

The invention can be used in an industrial water system. Such water systems would contain from about 0.05 to about 1000 ppm, more preferably from about 0.05 to about 10 ppm, and most preferably from about 0.1 to about 5 ppm of the stabilized aqueous solution of an alkali or alkaline earth metal hypobromite.

The invention can be used in the laundering of soiled garments where the soiled garments are washed in an aqueous media, such as water, containing a detergent and a bleaching agent. The stabilized aqueous solution of an alkali or alkaline earth metal hypobromite can be used as the bleaching agent.

The invention can also be used in the manufacture of cellulosic materials in which cellulosic fibers are bleached with an oxidizing agent. The stabilized aqueous solution of an alkali or alkaline earth metal hypobromite can be used as the oxidizing agent.

The invention can be used in the control of microbiofouling in a recreational water system in which an oxidizing agent is added to control microbiofouling. The stabilized aqueous solution of an alkali or alkaline earth metal hypobromite can be used as the oxidizing agent.

The invention can be used in the control of microbiofouling occurring on the surfaces of equipment in contact with produced oil field waters. An anti-microbiofouling effective amount of stabilized aqueous solution of an alkali or alkaline earth metal hypobromite can be added to the produced oil field waters.

The invention can also be used in the control of microbiofouling in aqueous systems. An effective anti-microbiofouling amount of stablized aqueous solution of an alkali or alkaline earth metal hypobromite can be added to aqueous systems.

In another embodiment the invention is a method of preventing microbiofouling on the surfaces of equipment in contact with in an industrial water system. The method comprises adding to the aqueous system an anti-microbiologically effective amount of a stabilized sodium hypobromite solution. The stabilized sodium hypobromite solution is prepared by the steps of:

a. Mixing an aqueous solution of sodium hypochlorite having from about 5 percent to about 30 percent available halogen (as chlorine) with sodium bromide;

b. Allowing the sodium bromide and the sodium hypochlorite to react to form a 0.5 to 30 percent by weight aqueous solution of unstabilized sodium hypobromite;

c. Adding to the unstabilized solution of sodium hypobromite an aqueous solution of an alkali metal sulfamate in a quantity to provide a molar ratio of alkali metal sulfamate to sodium hypobromite of from about 0.5 to about 7; and, d. Recovering a stabilized aqueous sodium hypobromite solution.

The industrial water systems include cooling water systems, cooling ponds, reservoirs, sweetwater applications, decorative fountains, pasteurizers, evaporative condensors, hydrostatic sterilizers and retorts, gas scrubber systems, and air washer systems.

Another embodiment of the invention is a method for preparing a stabilized aqueous alkali or alkaline earth metal hypobromite solution when the level of available halogen as chlorine is below about 5 percent. The method comprises the steps of:

a. Mixing an aqueous solution of alkali or alkaline earth metal hypochlorite [wherein the percent of available halogen (as chlorine) is less than about 5] with a water soluble bromide ion source;

b. Allowing the bromide ion source and the alkali or alkaline earth metal hypochlorite to react to form a 0.5 to 5 percent by weight aqueous solution of unstabilized alkali or alkaline earth metal hypobromite;

c. Adding to the unstabilized solution of alkali or alkaline earth metal hypobromite an aqueous solution of an alkali metal sulfamate having a temperature of at least 50° C. in a quantity to provide a molar ratio of alkali metal sulfamate to alkali or alkaline earth metal hypobromite is from about 0.5 to about 7; and, d. Recovering a stabilized aqueous alkali or alkaline earth metal hypobromite solution.

When the level of available halogen as chlorine is below about 5 percent, the amount of water in which the stabilizer, the alkali metal sulfamate, is dissolved into must be decreased. At this point, the amount of water is low enough that the alkali metal sulfamate is only sparingly soluble in the water. Therefore, the temperature of the aqueous alkali metal sulfamate solution must be maintained above 50° C. to keep the alkali metal sulfamate in solution until the solution is added to the aqueous solution of unstablized sodium hypobromite. Once mixed with the sodium hypobromite solution, solubility is no longer a concern, and the resulting stabilized sodium hypobromite solution solution does not need to be maintained above 50° C.

The alkali or alkaline earth metal hypochlorite is selected from the group consisting of sodium hypochlorite, potassium hypochlorite, magnesium hypochlorite, lithium hypochlorite, and calcium hypochlorite. The amount of hypochlorite used will vary depending upon which of the hypochlorite is used.

The bromide ion source is selected from the group consisting of sodium bromide, potassium bromide, lithium bromide, and hydrobromic acid. As shown in the examples, in a more preferred embodiment, the alkali or alkaline earth metal hypochlorite is sodium hypochlorite, the bromide ion source is sodium bromide, and the alkali or alkaline earth metal hypobromite is sodium hypobromite.

The aqueous solution of unstabilized alkali or alkaline earth metal hypobromite may contain from about 0.5 to about 70 percent by weight alkali or alkaline earth metal hypobromite, more preferably from about 1 to about 30 percent by weight alkali or alkaline earth metal hypobromite, and most preferably from about 4 to about 15 percent by weight alkali or alkaline earth metal hypobromite.

The pH of the stabilized aqueous alkali or alkaline earth metal hypobromite solution is from about 8 to about 14 and more preferably from about 11 to about 14. The the molar ratio of the alkali metal sulfamate to the sodium hypobromite is preferably from about 0.5 to about 7, more preferably from about 0.5 to about 4, and most preferrably from about 0.5 to about 2.

Another embodiment of the invention is a stabilized aqueous solution of an alkali or alkaline earth metal hypobromite which is prepared by the steps of:

a. Mixing an aqueous solution of alkali or alkaline earth metal hypochlorite [wherein the percent of available halogen (as chlorine) is less than about 5] with a water soluble bromide ion source;

b. Allowing the bromide ion source and the alkali or alkaline earth metal hypochlorite to react to form a 0.5 to 5 percent by weight aqueous solution of unstabilized alkali or alkaline earth metal hypobromite;

c. Adding to the unstabilized solution of alkali or alkaline earth metal hypobromite an aqueous solution of an alkali metal sulfamate having a temperature of at least 50° C. in a quantity to provide a molar ratio of alkali metal sulfamate to alkali or alkaline earth metal hypobromite is from about 0.5 to about 7; and, d. Recovering a stabilized aqueous alkali or alkaline earth metal hypobromite solution.

As discussed above, when the level of available halogen as chlorine is below about 5 percent, the amount of water in which the stabilizer, the alkali metal sulfamate, is dissolved into must be decreased. At this point, the amount of water is low that the alkali metal sulfamate is only sparingly soluble in the water. Therefore, the temperature of the aqueous alkali metal sulfamate solution must be maintained above 50° C. to keep the alkali metal sulfamate in solution until the solution is added to the aqueous solution of unstablized sodium hypobromite. Once mixed with the sodium hypobromite solution, solubility is no longer a concern, and the resulting stabilized sodium hypobromite solution solution does not need to be maintained above 50° C.

The alkali or alkaline earth metal hypochlorite is selected from the group consisting of sodium hypochlorite, potassium hypochlorite, magnesium hypochlorite, lithium hypochlorite, and calcium hypochlorite. The amount of hypochlorite used will vary depending upon which of the hypochlorite is used.

The bromide ion source is selected from the group consisting of sodium bromide, potassium bromide, lithium bromide, and hydrobromic acid. As shown in the examples, in a more preferred embodiment, the alkali or alkaline earth metal hypochlorite is sodium hypochlorite, the bromide ion source is sodium bromide, and the alkali or alkaline earth metal hypobromite is sodium hypobromite.

The aqueous solution of unstabilized alkali or alkaline earth metal hypobromite may contain from about 0.5 to about 70 percent by weight alkali or alkaline earth metal hypobromite, more preferably from about 1 to about 30 percent by weight alkali or alkaline earth metal hypobromite, and most preferably from about 4 to about 15 percent by weight alkali or alkaline earth metal hypobromite.

The pH of the stabilized aqueous alkali or alkaline earth metal hypobromite solution is from about 8 to about 14 and more preferably from about 11 to about 14. The the molar ratio of the alkali metal sulfamate to the sodium hypobromite is preferably from about 0.5 to about 7, more preferably from about 0.5 to about 4, and most preferrably from about 0.5 to about 2.

In another embodiment, the invention is a method of preventing microbiofouling on the surfaces of equipment in contact with in an industrial water system. The method comprises adding to the aqueous system an antimicrobiologically effective amount of a stabilized sodium hypobromite solution. The stabilized sodium hypobromite solution is prepared by the steps of:

a. Mixing an aqueous solution of sodium hypochlorite [wherein the percent of available halogen (as chlorine) is less than about 5] with sodium bromide;

b. Allowing the sodium bromide and the sodium hypochlorite to react to form a 0.5 to 5 percent by weight aqueous solution of unstabilized sodium hypobromite;

c. Adding to the unstabilized solution of sodium hypobromite an aqueous solution of an alkali metal sulfamate having a temperature of at least 50° C. in a quantity to provide a molar ratio of alkali metal sulfamate to sodium hypobromite of from about 0.5 to about 7; and, d. Recovering a stabilized aqueous sodium hypobromite solution.

As discussed above, when the level of available halogen as chlorine is below about 5 percent, the amount of water in which the stabilizer, the alkali metal sulfamate, is dissolved into must be decreased. At this point, the amount of water is low that the alkali metal sulfamate is only sparingly soluble in the water. Therefore, the temperature of the aqueous alkali metal sulfamate solution must be maintained at at least 50° C. to keep the alkali metal sulfamate in solution until the solution is added to the aqueous solution of unstablized sodium hypobromite. Once mixed with the sodium hypobromite solution, solubility is no longer a concern, and the resulting stabilized sodium hypobromite solution solution does not need to be maintained at at least 50° C.

Yet another embodiment of the application provides for the use of an alternative stabilizer to the aqueous alkali metal sulfamate. The contemplated stabilizer may be selected from the group consisting of acid amide derivatives of: carbonic acids, hydrogen cyanide, carboxylic acids, amino acids, sulfuric acids, phosphoric acids and boric acids. More specifically, the preferred stabilizers are selected from the group consisting of urea, thiourea, creatinine, cyanuric acids, alkyl hydantoins, mono or di ethanolamine, organic sulfonarnides, biuret, sulfamic acid, organic sulfamates and melamine. All of the stabilizers are compounds having an N—H or $NH_2$ group adjacent to an electron withdrawing functional group such as C=O, S=O, P=O, or B=O.

This invention provides several differences over the known art, including a specific order of addition in the manufacturing process whereby a stabilized sodium hypobromite solution is produced having improved stability, non-volatility, reduced bromate and AOX formation, improved microbiofouling control, and an increased free halogen residual in cooling water.

The stability of the stabilized hypobromite solution, as compared to the stabilized bromine disclosed in the Goodenough et al. reference and unstabilized sodium hypobromite in Table I, is greatly increased. Based on the surprising increased stability of the stabilized sodium hypobromite of this invention, it is apparent that the order of addition in the process of manufacture is critical.

TABLE I

INCREASED STABILITY OVER PRIOR ART
% LOSS OF AVAILABLE HALOGEN

| | After 4 days | After 14 days | After 21 days | After 34 days | After 84 days |
|---|---|---|---|---|---|
| Goodenough et al. | 21 | 23 | — | — | — |
| Stabilized Sodium Hypobromite | 0 | 0 | 0 | 1 | 1 |
| Unstabilized Sodium Hypobromite | — | 74 | 79 | 84 | 93 |

The chemical mechanism for halogen biocide stabilization by sulfamic acid has been proposed as follows:

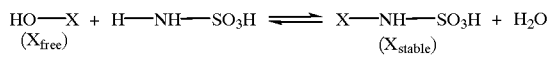

HO—X + H—NH—SO$_3$H ⇌ X—NH—SO$_3$H + H$_2$O
($X_{free}$)  ($X_{stable}$)

When X is Cl, the reaction applies to stabilized chlorine. When X is Br, the reaction applies to stabilized bromine.

The degree of stabilization is expressed as the concentration ratio of $X_{stable}$ to $X_{free}$. The $X_{free}$ concentration of the stabilized bromine was detectable while the concentration of the $X_{free}$ for stabilized chlorine was not. It was concluded that the chlorine in the stabilized chlorine was completely stabilized while the bromine in the stabilized bromine exists in both free and stabilized forms. This contributes in part to the increased antimicrobial properties of stabilized NaOBr over stabilized NaOCl which will be described in more detail in Example 3.

Absorbable organic halogen (AOX) is an important environmental parameter particularly in Europe. AOX can form from the reaction of some halogenated compounds with organics. The minimization of AOX by stabilizing NaOBr is a surprising benefit described in this disclosure.

Pathway A: AOX formation by HOX

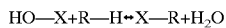

HO—X+R—H→X—R+H$_2$O

Where R—H can be the organic contaminants in cooling water or biomacromolecules and X—R is measured as AOX.

Pathway B:

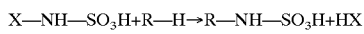

X—NH—SO$_3$H+R—H→R—NH—SO$_3$H+HX

This stabilized halogen reaction generates no X—R (AOX) as in Pathway A. When free chlorine (HOCl) or free bromine (HOBr) is used, AOX will be formed in accordance with the mechanism described by Pathway A.

When stabilized chlorine is used as a biocide, only Pathway B is possible because no free HOCl exists in the system. Thus, no or very low AOX will be formed using this product (see Table II below).

When stabilized bromine is used, both free and stabilized bromine forms coexist. Thus, both pathways A and B proceed and result in some AOX formation. However, the amount of AOX will be far less than when all of the halogen is in the form of free bromine (HOBr).

Apparently, the proposed mechanism explains the cause of AOX reduction due to the use of stabilized halogen biocides. The mechanism should be applicable to other stabilized halogen products when ammonia, amines or amides are used as the stabilizing agents.

In order to reduce the AOX formation by a stabilized halogen biocide, it is preferable to select strong stabilizing agents so that Pathway B can dominate. However, the drawback to a very stable halogenated compound is the generally decreased oxidation power that, in most cases, is directly correlated to its biocidal efficacy. Testing has shown that stabilized bromine is much more effective as a biocide than stabilized chlorine. Therefore, to reduce the AOX formation and at the same time maintain the compound's biocidal efficacy requires a well balanced selection of the stabilizing agent.

The following examples are presented to describe preferred embodiments and utilities of the invention and are not meant to limit the invention unless otherwise stated in the claims appended hereto.

EXAMPLE 1

Preparation of Stabilized Sodium Hypobromite with a Critical Order of Addition

In order to demonstrate the constancy of stabilized NaOBr, solutions of sodium hypochlorite and sodium bromide were mixed forming NaOBr then stabilized with sodium sulfamate as described below. Sodium hypochlorite solution was diluted in demand-free water. This diluted solution was titrated by the DPD-FAS method. The available chlorine level present in the original solution was determined to be 15 percent. 42.4 grams of the neat NaOCl solution were added to 20.5 grams of a 45 percent NaBr solution. This reaction forms unstabilized NaOBr. The stabilization solution was formulated with 9.6 grams of sulfamic acid, 14 grams of water, and 13.2 grams of 50 percent sodium hydroxide. The stabilization solution is then added with stirring to the NaOBr. The order of addition is critical in this process which differs from the Goodenough et al. reference. For instance, if the stabilizer was added to NaOCl prior to NaBr introduction, the bromide would not be oxidized to hypobromite. Also, bromine solutions prepared in the manner referenced above gave more stable oxidizing species than the prior art. Bromine solutions stabilized as explained in the Goodenough et al. reference exhibited a decrease in halogen activity from an initial concentration of 1 percent to 0.77 percent after fourteen days representing an active ingredient loss of 23 percent. The stabilization procedure described here improved on the prior art as the decline of active ingredient was only 1 percent after 84 days (see Table I above). An unstabilized NaOBr solution prepared in an similar process by replacing sulfamic acid with distilled water lost 94 percent available halogen during the same period.

EXAMPLE 2
Less AOX is Formed in Stabilized Halogen Solutions

AOX is a generic class of compounds which includes all organic molecules containing halogen. Limits for AOX discharge from cooling water systems have already been established in some European countries. To simulate AOX formation during stabilized and unstabilized sodium hypobromite action in cooling water, a mixed bacterial culture typically found in cooling water was cultivated in L-broth overnight and the cells harvested by centrifugation. The cell pellet was washed with synthetic cooling water (90 ppm calcium, 50 ppm magnesium, 110 ppm "M" alkalinity, pH 8.0–8.2) twice to remove the remaining organic medium. Cells were then resuspended into an equal volume of cooling water. A capped dark bottle served as the reactor. Synthetic cooling water was added to the bottle followed by the washed bacterial stock yielding approximately $10^7$ cells/ml. Stabilized NaOBr or unstabilized NaOBr was dosed into this bacterial suspension at a final concentration of 1, 2, 3, or 4 ppm total halogen (as chlorine). Headspace in the bottle was minimized to avoid the evaporative loss of halogenated organics and the solution stirred for 24 hours to simulate a typical cooling system. Immediately before AOX analysis, the sample was acidified to pH 2.0 with concentrated nitric acid. A Mitsubishi TOX-10 Analyzer was used according to US EPA Method 9020 to measure the AOX concentration in the samples. Ultrapure water was used for the preparation of all reagents and standard solutions to prevent any contamination. The amounts of AOX formed in each such treatment is shown in Table II below. Cooling water with stabilized NaOBr formed less AOX than treatments using unstabilized NaOBr at equivalent halogen concentrations. Linear regressions were performed on both sets of data to obtain linear-fit equations shown below for both stabilized and unstabilized NaOBr:

Stabilized NaOBr: AOX (ppb)=23.3×Dose (ppm)

Unstabilized NaOBr: AOX (ppb)=53.9×Dose (ppm)

Testing also showed that stabilization of NaOCl reduced AOX generation in cooling water dosed with two ppm total residual (see Table II).

TABLE II

AOX FORMATION (ppb) IN STABILIZED HALOGEN SOLUTIONS

| DOSE | ppb AOX Formed from Specified Halogen Source | | | |
|---|---|---|---|---|
| (ppm total halogen as chlorine) | Stabilized NaOBr | Unstabilized NaOBr | Stabilized NaOCl | Unstabilized NaOCl |
| 1 | 29 | 56 | | |
| 2 | 52 | 124 | 13 | 118 |
| 3 | 68 | 174 | | |
| 4 | 91 | 197 | | |

EXAMPLE 3
Antibacterial Activity of Stabilized Sodium Hypobromite

Freshly prepared solutions of stabilized and unstabilized sodium hypobromite were diluted then added to cooling water in order to achieve a one ppm free halogen residual (as chlorine). Sodium hypochlorite was stabilized in the same fashion as described for NaOBr in Example One with the exception that NaBr was directly replaced with distilled water. Stabilized and unstabilized sodium hypochlorite were diluted then added to cooling water at a final concentration of one ppm free halogen residual (as chlorine). The volumes of all solutions needed to achieve a one ppm free halogen residual (as chlorine) was recorded. Following 6 and 21 days of dark storage, identical dilutions of stabilized and unstabilized sodium hypohalite solutions were prepared and the volume originally required for a one ppm free halogen residual (as chlorine) was added to cooling water containing approximately $10^6$ Pseudomonas aeruginosa cells/mL. Aliquots were extracted at 10 and 30 minutes into cooling water dilution blanks containing a halogen neutralizer (0.05 percent $Na_2S_2O_3$) then enumerated on tryptone glucose extract agar. Stabilized NaOBr retained its antibacterial activity after storage while the unstabilized form lost its efficacy against Pseudomonas aeruginosa (see Table III below). The results were even more dramatic as the storage period increased. This effect was likely due to the disproportionation of the unstable hypobromite ion into the non-biocidal species bromide and bromate. Surprisingly, NaOCl stabilized in the same manner as NaOBr was comparatively ineffective under the conditions tested (Table III).

TABLE III

ANTIBACTERIAL ACTIVITIES OF STABILIZED & UNSTABILIZED HYPOHALITE SOLUTIONS AFTER 6 & 21 DAYS
equivalent volumes initially required to achieve one ppm free halogen added throughout test

| | % BACTERIA KILLED | | | |
|---|---|---|---|---|
| | 6 DAYS OF STORAGE CONTACT TIME (MINUTES) | | 21 DAYS OF STORAGE CONTACT TIME (MINUTES) | |
| | 10 | 30 | 10 | 30 |
| stabilized NaOBr | 99.9 | 100 | 99.8 | 100 |
| unstabilized NaOBr | 99.8 | 99.7 | 0.4 | 6.1 |
| stabilized NaOCl | 0 | 0 | 0 | 21.0 |
| unstabilized NaOCl | 100 | 100 | 100 | 100 |

EXAMPLE 4
Depression of Bromate Formation Following Stabilization of Sodium Hypobromite Hypohalite ions are known to disproportionate into halate and halide under alkaline conditions. Halate ions are undesirable degradants being suspect carcinogens and are under consideration for governmental regulation. The reaction of NaBr with NaOCl can yield significant amounts of bromate in elevated pH environments. Surprisingly, the stabilization of NaOBr with sodium sulfamate greatly minimized bromate formation (see Table IV below). Stabilized and unstabilized sodium hypobromite solutions were prepared as described in Example One. These solutions were stored in the dark at room temperature during the course of the study. Eight month old samples of stabilized and unstabilized NaOBr, both maintained at pH 14, a condition suitable for bromate formation, were assayed for bromate. A Dionex 4000 series gradient ion chromatography system equipped with AG9-SC/AS9-SC columns and a conductivity detector was used to measure the bromate concentration in the samples. The chromatograph was operated according to a method currently under investigation by the EPA for the analysis of bromate in ozonated drinking water. Purified water from an Interlake Water Systems deionization system was used for the preparation of all reagents and standard solutions to prevent contamination.

TABLE IV

BROMATE FORMATION IN STABILIZED & UNSTABILIZED
NaOBr SOLUTIONS STORED FOR EIGHT MONTHS

|  | STABILIZED NaOBr | UNSTABILIZED NaOBr |
|---|---|---|
| PERCENT BROMATE | 0.004 | 2.700 |

As noted above, the pH of these solutions was high which favors bromate formation. However, NaOCl, which contains significant amounts of NaOH, is typically diluted with System water prior to the introduction of the bromide species in most industrial applications. The pH of this diluted system would be lower than the neat NaOCl/NaBr formulation described above theoretically minimizing bromate formation. The available chlorine in a NaOCl sample diluted (1:100) with distilled water was titrated by the DPD-FAS method. A solution of 45 percent sodium bromide was added to the dilute NaOCl at a molar ratio of 1 $Cl_2$:1 $Br^-$ forming NaOBr. This reaction proceeded for thirty minutes. Then, appropriate volumes of this dilute NaOBr solution were added to cooling water (pH 8.3) giving total available halogen levels of 1, 2, 3, and 4 ppm (as $Cl_2$) as determined by the DPD-FAS method. Similarly, a dilution of stabilized sodium hypobromite (1: 100) was made in distilled water. Dilute stabilized NaOBr was added to cooling water (pH 8.3) giving total available halogen levels of 1, 2, 3, and 4 ppm (as $Cl_2$) as determined by the DPD-FAS method. Bromate analysis then proceeded in the manner described above. Bromate was not detected in any of the cooling water samples dosed with either stabilized or unstabilized dilute NaOBr at typical use concentrations. These results signify the safety factor for bromate built into the stabilized sodium hypobromite formulation as well as the industrial in situ oxidation of NaBr with dilute NaOCl.

EXAMPLE 5
Use of Stabilized NaOBr Increased the Percentage of Free Residual in a Recirculating Cooling Water System Compared to Other Stabilized Halogen Compounds A major drawback to some commercial stabilized chlorine products for industrial water treatment is the low percentage of free chlorine residual delivered to the water system. This effect is due to the strength of the chemical bond between the stabilizer usually a nitrogenous compound, and chlorine. Chloramines, ie. combined chlorine, are weaker microbicides than free chlorine. However, bromamines are considered to be nearly as effective against microorganisms as free bromine. Thus, it is essential to have a high percentage of the total available halogen in the free form when chlorine products are employed. Conversely, this phenomenon is not as crucial when employing stabilized NaOBr. A commercial heating, ventilation and air conditioning ("HVAC") cooling system was sequentially treated with stabilized NaOCl, a bromochloroalkylhydantoin, and finally stabilized NaOBr. There was a low percentage of free chlorine relative to total available halogen present in the stabilized NaOCl treated system (see Table V below). A lower percentage of free halogen was measured when a different stabilization system, an alkylhydantoin, was employed with bromine and chlorine (see Table V below). However, when stabilized NaOBr was fed into this system, the percentage of free available halogen relative to the total residual measured quickly increased (see Table V below). These phenomena imply that less stabilized NaOBr is required to obtain a free available halogen residual than the equivalent amount of stabilized NaOCl.

TABLE V

FREE RESIDUAL OXIDANT AS A PERCENT OF TOTAL RESIDUAL
OXIDANT IN RECIRCULATING COOLING WATER SYSTEM

| Days in System | Average Free Oxidant as a Percent of Total Residual Oxidant | Biocide Employed |
|---|---|---|
| 36 | 13 | stabilized NaOCl |
| 45 | 9 | halogenated hydantoins |
| 33 | 53 | stabilized NaOBr |

EXAMPLE SIX
Stabilization of Sodium Hypobromite Reduces Volatility

If a biocide is highly volatile, its performance may be adversely affected. For example, the biocide may flash off in the highly aerated conditions of a cooling tower or an air washer. This would lower the biocide concentration in the cooling water wasting the product. Halogen volatility also leads to vapor-phase corrosion of susceptible equipment surfaces. In addition halogen volatility may cause worker discomfort due to the "swimming pool" aroma. Thus, the need for an efficacious oxidizing biocide with low volatility is evident.

Concentrated solutions of either NaOCl, NaOBr, or stabilized NaOBr were added to a beaker. Halogen vapors were detected from the NaOCl and NaOBr solutions. No odors were noticed from the stabilized NaOBr. This is an improvement over existing products by minimizing halogen odors in product storage areas.

Bleach, NaOCl, is not commonly used in air washer systems due to some of the reasons listed above. Once an effective microbial control dose is achieved, the halogen odor may be so overwhelming that workers would not be able to comfortably operate in the treated areas. The low volatilization of stabilized NaOBr overcomes this drawback. Stabilized sodium hypobromite was added at elevated use concentrations to two textile mill air washers in order to investigate its volatility. Then the air was monitored throughout the mill. A Sensidyne air monitoring device outfitted with halogen detection tubes was used to instantaneously detect halogen in the air. The lower detection limit was 50 ppb which is below the Threshold Limit Value-Short Term Exposure Limit for bromine as established by OSHA. In addition halogen badges were placed throughout textile mills in order to detect halogen vapors over extended periods of time. Neither monitoring system detected any halogen present in the air following the elevated stabilized NaOBr dose. No halogen odors were encountered in either the air washer unit or the return air. The microbial population was enumerated before and after stabilized NaOBr addition. The microbial population following dosing was reduced by greater than one order of magnitude. This example demonstrates the utility of stabilized sodium hypobromite in controlling the bacterial population while adding no halogen odor to the system area.

Changes can be made in the composition, operation and arrangement of the method of the present invention described herein without departing from the concept and scope of the invention as defined in the following claims:

What is claimed is:

1. In a method for the laundering of soiled garments in which the soiled garments are washed in an aqueous media containing a detergent and a bleaching agent, the improvement comprises using as the bleaching agent a stabilized aqueous alkali or alkaline earth metal hypobromite solution prepared by the following steps:

a. mixing an aqueous solution of alkali or alkaline earth metal hypochlorite having from about 5 percent to about 70 percent by weight available halogen as chlorine with a water soluble bromide ion source;

b. allowing the bromide ion source and the alkali or alkaline earth metal hypochlorite to react to form a 0.5 to 70 percent by weight aqueous solution of unstabilized alkali or alkaline earth metal hypobromite:

c. adding to the unstabilized solution of alkali or alkaline earth metal hypobromite a stabilizer selected from the group consisting of an alkali metal sulfamate, carbonic acids, hydrogen cyanide, carboxylic acids, amino acids, sulfuric acids, phosphoric acids and boric acids; and, d. recovering a stabilized aqueous alkali or alkaline earth metal hypobromite solution.

2. In a method for the manufacture of cellulosic materials in which cellulosic fibers are bleached with an oxidizing agent, the improvement comprises using as the oxidizing agent a stabilized aqueous alkali or alkaline earth metal hypobromite solution prepared by the following steps:

a. mixing an aqueous solution of alkali or alkaline earth metal hypochlorite having from about 5 percent to about 70 percent by weight available halogen as chlorine with a water soluble bromide ion source;

b. allowing the bromide ion source and the alkali or alkaline earth metal hypochlorite to react to form a 0.5 to 70 percent by weight aqueous solution of unstabilized alkali or alkaline earth metal hypobromite;

c. adding to the unstabilized solution of alkali or alkaline earth metal hypobromite a stabilizer selected from the group consisting of an alkali metal sulfamate, carbonic acids, hydrogen cyanide carboxylic acids, amino acids, sulfuric acids, phosphoric acids and boric acids; and, d. recovering a stabilized aqueous alkali or alkaline earth metal hypobromite solution.

3. In a method for the control of microbiofouling in a recreational water system in which an oxidizing agent is added to control microbiofouling, the improvement comprises using as the oxidizing agent a stabilized aqueous alkali or alkaline earth metal hypobromite solution prepared by the following steps:

a. mixing an aqueous solution of alkali or alkaline earth metal hypochlorite having from about 5 percent to about 70 percent by weight available halogen as chlorine with a water soluble bromide ion source;

b. allowing the bromide ion source and the alkali or alkaline earth metal hypochlorite to react to form a 0.5 to 70 percent by weight aqueous solution of unstabilized alkali or alkaline earth metal hypobromite;

c. adding to the unstabilized solution of alkali or alkaline earth metal hypobromite a stabilizer selected from the group consisting of an alkali metal sulfamate, carbonic acids, hydrogen cyanide, carboxylic acids, amino acids, sulfuric acids, phosphoric acids and boric acids; and, d. recovering a stabilized aqueous alkali or alkaline earth metal hypobromite solution.

4. In a method for the control of microbiofouling occurring on the surfaces of equipment in contact with produced oil field waters, the improvement comprises adding to the produced oil field waters an anti-microbiofouling effective amount of a stabilized aqueous alkali or alkaline earth metal hypobromite solution prepared by the following steps:

a. mixing an aqueous solution of alkali or alkaline earth metal hypochlorite having from about 5 percent to about 70 percent by weight available halogen as chlorine with a water soluble bromide ion source;

b. allowing the bromide ion source and the alkali or alkaline earth metal hypochlorite to react to form a 0.5 to 70 percent by weight aqueous solution of unstabilized alkali or alkaline earth metal hypobromite;

c. adding to the unstabilized solution of alkali or alkaline earth metal hypobromite a stabilizer selected from the group consisting of an alkali metal sulfamate, carbonic acids, hydrogen cyanide, carboxylic acids, amino acids, sulfuric acids, phosphoric acids and boric acids; and, d. recovering a stabilized aqueous alkali or alkaline earth metal hypobromite solution.

5. A method of controlling microbiofouling in an aqueous system which comprises adding to the aqueous system an effective, anti-microbiofouling amount of a stabilized aqueous alkali or alkaline earth metal hypobromite solution prepared by the following steps:

a. mixing an aqueous solution of alkali or alkaline earth metal hypochlorite having from about 5 percent to about 70 percent by weight available halogen as chlorine with a water soluble bromide ion source;

b. allowing the bromide ion source and the alkali or alkaline earth metal hypochlorite to react to form a 0.5 to 70 percent by weight aqueous solution of unstabilized alkali or alkaline earth metal hypobromite;

c. adding to the unstabilized solution of alkali or alkaline earth metal hypobromite a stabilizer selected from the group consisting of an alkali metal sulfamate, carbonic acids, hydrogen cyanide, carboxylic acids, amino acids, sulfuric acids, phosphoric acids and boric acids; and, d. recovering a stabilized aqueous alkali or alkaline earth metal hypobromite solution.

6. A method of preventing microbiofouling on the surfaces of equipment in contact with in an industrial water system which comprises adding to the aqueous system an anti-microbiologically effective amount of a stabilized sodium hypobromite solution, said solution having been prepared by the steps of:

a. mixing an aqueous solution of alkali or alkaline earth metal hypochlorite having from about 5 percent to about 70 percent by weight available halogen as chlorine with a water soluble bromide ion source;

b. allowing the bromide ion source and the alkali or alkaline earth metal hypochlorite to react to form a 0.5 to 70 percent by weight aqueous solution of unstabilized alkali or alkaline earth metal hypobromite;

c. adding to the unstabilized solution of alkali or alkaline earth metal hypobromite a stabilizer selected from the group consisting of an alkali metal sulfamate, carbonic acids, hydrogen cyanide, carboxylic acids, amino acids, sulfuric acids, phosphoric acids and boric acids; and, d. recovering a stabilized aqueous alkali or alkaline earth metal hypobromite solution.

7. The method according to claim 6, wherein the industrial water system is selected from a group consisting of: a cooling water system; a sweetwater system; a gas scrubber system; and, an air washer system.

8. The method of claim 6, wherein the stabilizer is selected from the group consisting of urea, thiourea, creatinine, cyanuric acids, alkyl hydantoins, mono or di ethanolamine, organic sulfonamides, biuret, sulfamic acid, organic sulfamates and melamine.

* * * * *